United States Patent

Hakamatsuka

Patent Number: 5,346,396
Date of Patent: Sep. 13, 1994

[54] DENTAL PROSTHESIS

[75] Inventor: Yasuharu Hakamatsuka, Tokyo, Japan

[73] Assignee: Olympus Optical Co., Ltd., Tokyo, Japan

[21] Appl. No.: 15,643

[22] Filed: Feb. 9, 1993

[30] Foreign Application Priority Data

Feb. 19, 1992 [JP] Japan .................................. 4-031920

[51] Int. Cl.$^5$ ............................................ A61C 13/08
[52] U.S. Cl. .................................. 433/208; 433/202.1
[58] Field of Search ..................... 433/202.1, 206, 207, 433/208, 218, 222.1, 223

[56] References Cited

U.S. PATENT DOCUMENTS

| | | | |
|---|---|---|---|
| 4,129,944 | 12/1978 | Sung et al. | 433/207 |
| 4,451,236 | 5/1984 | Tarasov et al. | 433/207 |
| 4,585,417 | 4/1986 | Sozio et al. | 433/202.1 |
| 4,799,887 | 1/1989 | Hakamatsuka et al. | |
| 4,828,495 | 5/1989 | Bell et al. | 433/200.1 |
| 5,176,747 | 1/1993 | Panzera et al. | 106/35 |

FOREIGN PATENT DOCUMENTS

0468435A2  1/1992  European Pat. Off. .

OTHER PUBLICATIONS

English language Abstract of JP 4-231060.

Primary Examiner—Gene Mancene
Assistant Examiner—Cindy A. Cherichetti
Attorney, Agent, or Firm—Frishauf, Holtz, Goodman & Woodward

[57] ABSTRACT

A wax pattern is built up on the surface of the other end of a post comprising pure titanium. The wax pattern is used to produce a casting mold. While the casting mold is kept at a predetermined temperature, a crystallized glass having a thermal expansion coefficient falling within the range of $\pm 5 \times 10^{-7}$ with respect to that of pure titanium is melted and cast in the mold. The resultant mold product is heated and crystallized to obtain a dental prosthesis. A post comprising pure titanium is chemically bonded to a core comprising the crystallized glass. This invention provides a dental prosthesis which is easy to manufacture and nontoxic to the human body.

11 Claims, 1 Drawing Sheet

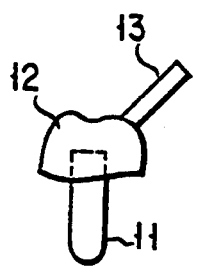
F I G. 1A
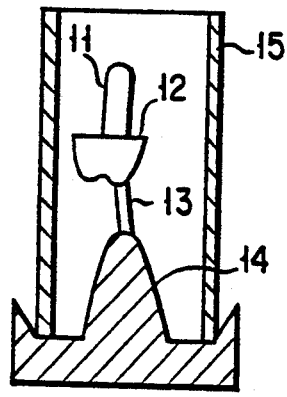
F I G. 1B
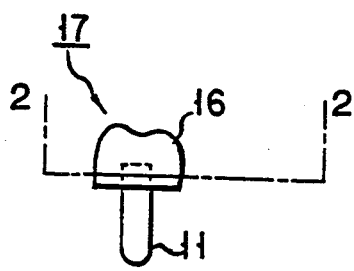
F I G. 1C
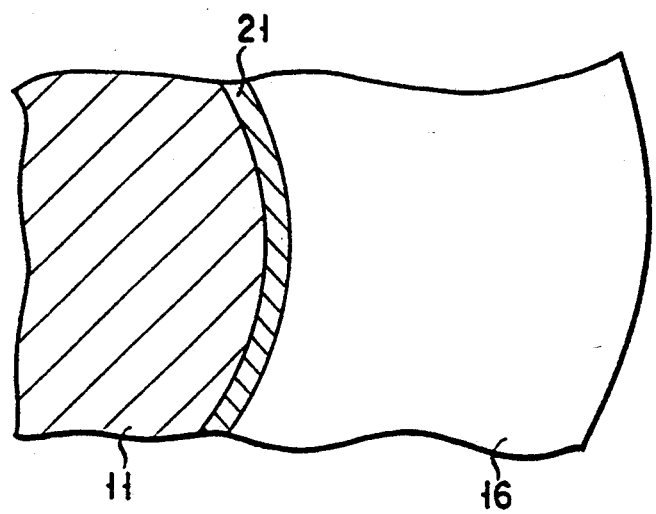
F I G. 2

DENTAL PROSTHESIS

BACKGROUND OF THE INVENTION

1. Field of the Invention

The present invention relates to a dental prosthesis and, more particularly, to a dental prosthesis which is easy to manufacture and nontoxic to the human body.

In addition, the present invention relates to a method of manufacturing the dental prosthesis.

2. Description of the Related Art

Dental prosthesis have been used to restore diseased and missing teeth. As a conventional dental prosthesis, a porcelain such as VITADUR (manufactured by VITA Co. Ltd.) or DUCERAM (manufactured by DUCERA Co. Ltd.) is built up on a post comprising a base metal (e.g., a nickel-cobalt alloy or a cobalt-chromium alloy), a noble metal (e.g., gold or platinum), or an alloy of the base and noble metals, and the resultant body is calcined and heated to obtain a metal fused porcelain crown as a so-called metal bond.

However, in a conventional metal fused porcelain crown, the porcelain must be repeatedly built up on the post to modify the shape until a desired shape is obtained. The manufacture each dental prosthesis consumes therefore much of time.

The most frequently used base metal as a metal constituting the post has a high ionization tendency, and metal ions tend to be eluted. Even if an alloy containing a noble metal is used, a galvanic action between the heterogeneous metals occurs in the oral cavity, so that metal ions tend to be eluted. It is known that the eluted metal ions cause allergic diseases to specific people.

SUMMARY OF THE INVENTION

The present invention has been made in consideration of the above situation, and has as its object to provide a dental prosthesis which is easy to manufacture and nontoxic to the human body.

The present inventors have made extensive studies and have found that the above object can be achieved by a dental prosthesis using a combination of a titanium-based metal nontoxic to the human body and a glass ceramics in moldability, thus establishing the present invention.

More specifically, according to the present invention, there is provided a dental prosthesis comprising a substrate body comprising titanium-based metal and a molding body comprising a glass ceramic and molded on a part of the substrate body to form a shape corresponding to at least to a crown, the glass ceramic having a thermal expansion coefficient falling within a range of $\pm 5 \times 10^{-7}$ with respect to that of the titanium-based metal, wherein the molding body is chemically bonded to the substrate body.

In addition, the present invention provides a method of manufacturing of a dental prosthesis comprising the following steps of: (a) building up a wax pattern to a desirable shape on a substrate body comprising titanium-based metal, (b) surrounding the wax pattern and the substrate body with a frame means, (c) pouring a molding material into cavity defined by the wax pattern thereby, the substrate body and the frame means bury the wax pattern in the molding material, (d) obtaining a mold by calcining the molding material a make to lost wax pattern so as to form a cavity having a shape corresponding to the wax pattern, (e) casting a melted glass ceramic into the mold while the mold is kept heated at a predetermined temperature to obtain a mold product in which the glass ceramic is chemically bonded to the substrate body, and, (f) subjecting the glass ceramic to a crystallizing treatment by heating the mold product at a predetermined temperature.

The dental prosthesis according to the present invention will be described in detail.

In the dental prosthesis according to the present invention, the substrate body comprising a titanium-based metal is used. The titanium-based metal is, for example, pure titanium coated with titanium oxide. In general, the surface of pure titanium is oxidized to be titanium oxide. It is known that titanium oxide is safe against to the human body (Akio Makishima & Hideki Aoki, Bioceramics, Bioreactions against various types of ceramics, Gihodo Publishing Co., 1984, P. 46—46). Pure titanium coated with titanium nitride or titanium carbonitrate can also be used. Such a titanium material can improve the metal color on the surface of pure titanium or titanium oxide and can also adjust the thermal expansion coefficient of titanium.

The glass ceramic has used in the dental prosthesis according to the present invention has a thermal expansion coefficient falling within the range of $\pm 5 \times 10^{-7}$ with respect to that of the titanium-based metal. When the glass ceramic having a thermal expansion coefficient falling outside the above range is used, bonding between the titanium-based metal and the glass ceramic becomes incomplete. The resultant material cannot have a sufficiently high mechanical strength as a dental prosthesis.

In the dental prosthesis according to the present invention, the molding body comprising the glass ceramic is chemically bonded to the substrate body comprising the titanium-based metal. The expression "chemically bonded" means that oxygen atoms in the titanium oxide layer formed on the surface of pure titanium or oxygen atoms in the surface of the glass ceramic are bonded to titanium atoms of the corresponding titanium oxide layer or silicon atoms on the surface of the glass ceramic, thereby forming strong bonds between the respective layers.

The chemical bond between the titanium-based metal and the glass ceramic can be formed by heating while the substrate body is kept in contact with the molding body. When the titanium-based metal is heated at a temperature of, e.g., 700° C. to 900° C., an oxide layer can be formed on the surface of the heated titanium-based metal. Melted glass (containing various types of anions) is brought into tight contact with the surface of the oxide layer by centrifugal casting. At this time, the chemical reaction between the oxide layer and the glass layer is enhanced by pressure in centrifugal casting, so that the chemical bond between the oxide layer and the glass layer can be obtained.

More specifically, at least part of the substrate body comprising the titanium-based metal can be placed in a casting mold having a cavity with a predetermined shape, and the melted glass ceramic can be cast in the casting mold. The chemical bonds can be formed between the titanium-based metal and the glass ceramic by the temperature inside the casting mold.

Alternatively, a powder of the glass ceramics may be molded in a predetermined shape so as to contain at least part of the substrate body. The molded body may be compressed at a predetermined pressure and then calcined at a predetermined temperature, thereby being able to form chemical bonds between the titanium-based metal and the glass ceramic.

Alternatively, a titanium-based metal may be, for example, RF-heated while the glass ceramic is kept in contact with the titanium-based metal, thereby being able to form chemical bonds between the titanium-based metal and the glass ceramic.

The shape of the substrate body used in combination with the molding body consisting of the glass ceramic is not limited to a specific one if a necessary mechanical strength is imparted to the molding body as a dental prosthesis. For example, the substrate body may be a post for supporting a core consisting of a glass ceramic cast in the form of a crown. The substrate body may be a wire used as a skeleton of a normal molding body for a prosthesis.

In the dental prosthesis according to the present invention, since the substrate body comprising the titanium-based metal having a sufficiently high mechanical strength and nontoxic to the human body is strongly bonded to the molding body comprising a glass ceramic, having a high biological affinity and excellent in moldability, by means of the chemical bonds, the dental prosthesis can easily be cast in a desired shape and has a sufficiently high mechanical strength, thereby being able to facilitate the manufacture of the dental prosthesis and minimize a toxic influence on the human body.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitutes a part of the specification, illustrates a presently preferred embodiment of the invention and, together with the general description given above and the detailed description of the preferred embodiment given below, serves to explain the principles of the invention.

FIGS. 1A to 1C are views for explaining the steps in manufacturing a dental prosthesis according to the present invention; and FIG. 2 is a view for explaining a bonded state between a core and a post in a dental prosthesis according to an embodiment of the present invention.

DETAILED DESCRIPTION OF THE PREFERRED EMBODIMENTS

Preferred embodiments of the present invention will be described in detail with reference to the accompanying drawings.

EXAMPLE 1

FIGS. 1A to 1C are views for explaining the steps in manufacturing a dental prosthesis according to the present invention.

The end of a pure titanium round rod (Kobe Seitetsujyo, Class 1; diameter: 3 mm; length: 20 mm; thermal expansion coefficient (to be referred to as "$\alpha$" hereinafter)$=8.5\times10^{-6}$) was chamfered to prepare a post 11. A wax pattern 12 was built up on the surface of the other end of the post 11 to have a desired shape. A sprue line 13 consisting of a wax was mounted at a predetermined portion of the wax pattern 12.

The wax pattern 12 thus obtained was set up on the end of a projection of a crucible former 14 through the sprue line 13, as shown in FIG. 1B. Thereafter, a metal ring 15 was placed on the peripheral portion of the crucible former 14 so as to surround the post 11, the wax pattern 12, the sprue line 13, and the projection of the crucible former 14.

A slurry-like phosphate-bonded investment for casting was poured into the metal ring 15 to bury completely the post 11 in the investment. After the investment was perfectly solidified, the crucible former 14 was removed and the investment was calcined at a predetermined temperature, thereby calcining the investment and making a lost the wax pattern 12 and sprue line 13. As a result, a casting mold having a cavity whose shape corresponds to the wax pattern 12 including the other end of the post 11 was obtained.

While the resultant casting mold was kept heated at about 575° C., a glass ceramic [Olympus Castable Ceramics (available from OLYMPUS OPTICAL CO., LTD.); $\alpha=8.2\times10^{-6}$; having both a mica crystal and a $\beta$-spodumene crystal precipitate after crystallization (to be referred to as an OCC hereinafter)] was melted in a melting cast furnace for the glass ceramic, and the melted glass ceramic was cast in the casting mold. After completion of casting, a cast product was removed after cooling of the casting mold. In the resultant mold product, the post 11 was chemically bonded to a core 16 consisting of the OCC.

The mold product was heated and crystallized at 880° C. to 900° C. to obtain a finished dental prosthesis 17, as shown in FIG. 1C. The resultant dental prosthesis 17 was cut along the line 2—2 in FIG. 1C, and the sectional surface was observed with an optical microscope ($\times 5$). It was confirmed that the post 11 and the core 16 were sufficiently chemically bonded through a titanium-OCC diffusion layer 21, as shown in FIG. 2. A titanium oxide layer was formed on the surface of the core 16 and exhibited a metallic color.

EXAMPLE 2

After the surface of a pure titanium round rod as in Example 1 was degreased and cleaned, the resultant rod was placed in a titanium nitride layer forming apparatus to form a titanium nitride layer having a thickness of about 1 $\mu$m on the surface of the rod. A mold product was obtained following the same procedures as in Example 1, except that the above pure titanium round rod covered with titanium nitride was used. The post and core of the resultant mold product in Example 2 were chemically bonded as in Example 1.

The cast product was crystallized following the same procedures as in Example 1 to obtain a dental prosthesis. The resultant dental prosthesis was cut, and the sectional surface was observed. It was confirmed as in Example 1 that the post and core were sufficiently chemically bonded to each other. Since the surface of the post was covered with titanium nitride in the dental prosthesis of Example 2, it exhibited a gold color. It was confirmed that the dental prosthesis was more excellent in an aesthetic sense than the dental prosthesis of Example 1 in which titanium oxide was directly exposed and exhibited a metallic color.

EXAMPLE 3

States of chemical bonds between a titanium-based metal and various types of glass ceramics upon changes in thermal expansion coefficients in the glass ceramics are examined in Example 3.

A porcelain ($\alpha = 8.0 \times 10^{-6}$) having a thermal expansion coefficient slightly smaller than that of pure titanium was fused onto a bridge base tooth consisting of pure titanium ($\alpha = 8.5 \times 10^{-6}$) at about 780° C. A wax pattern was built up on the resultant bridge base tooth, and each casting mold was formed following the same procedures as in Example 1. After the OCC ($\alpha = 8.2 \times 10^{-6}$) of Example 1, glass ceramic I ($\alpha = 8.0 \times 10^{-6}$), and glass ceramics II ($\alpha = 12.0 \times 10^{-6}$) were melted, the melted materials were cast in the resultant three casting molds and crystallized, respectively. Herein, the temperature of each casting mold was changed depending on the type of the glass ceramic. The bonded states of the molding body of Example 3 and Comparative Examples 1 and 2 with titanium, and the oxidized states of titanium were examined. Results are shown in Table 1 below.

TABLE 1

| | Thermal Expansion Coefficient of Ceramics ($\alpha$) | Temperature of Casting Mold (°C.) | State of Molding body Bonded to Ti | Oxidized State on Surface of Ti |
|---|---|---|---|---|
| Example 3 | $8.2 \times 10^{-6}$ | 550° C. | Good | Proper |
| Comparative Example 1 | $8.0 \times 10^{-6}$ | about 900° C. | Fair | Improper |
| Comparative Example 2 | $12.0 \times 10^{-6}$ | 550° C. | Unsatisfactory | Proper |

As is apparent from Table 1, the state of the molding body using the OCC according to the present invention, thus, Example 1, bonded with titanium and the oxidized state of titanium were good and proper, respectively. However, although the ceramic portion of the dental prosthesis of Comparative Example 1 was not destroyed, the titanium-based metal was oxidized to the inside and considerably modified because the temperature of the casting mold was as high as 900° C. The ceramic portion of the dental prosthesis of Comparative Example 2 was destroyed, and no chemical bond was formed between the titanium-based metal and the glass ceramic.

From the above test results, it is found that the temperature of the casting mold is preferably set at a temperature which does not cause oxidation of pure titanium and that the thermal expansion coefficient of the ceramic is preferably as close as that of the titanium-based metal.

EXAMPLE 4

A skeleton having a predetermined shape was formed using a titanium soft wire having a diameter of about 0.1 mm. Thereafter, a rectangular wax pattern having dimensions of 3×4×40 mm was formed on the skeleton using a wax. A sprue line using the same wax as the wax pattern was mounted on the resultant wax pattern. A casting mold was formed following the same procedures as in Example 1, except that the above wax pattern including the skeleton was used. The resultant casting mold had a cavity having the shape corresponding that of the wax pattern, and including a skeleton consisting of the titanium soft wire.

While this casting mold was maintained at about 575° C., the melted OCC used as in Example 1 was cast in the casting mold with centrifugal, thereby casting the OCC. The resultant mold product was crystallized under the same conditions as in Example 1, thereby obtaining a sample incorporating the titanium soft wire. On the other hand, a sample of Comparative Example 4 was produced following the same procedures as described above, except that the titanium soft wire was not incorporated. The bending strength was examined and the fracture of these samples after the examination was observed.

The sample of Example 4, i.e., incorporating the skeleton, had a bending strength of 3,500±500 kg/cm. Even if the sample was damaged, fractures were not considerably scattered. To the contrary, the sample of Comparative Example 4, i.e., having no skeleton had a bending strength of 2,400±450 kg/cm, and fractures were scattered around.

From the above results, it was confirmed that the dental prosthesis of Example 4 has a higher bending strength (1.5 times) than that of Comparative Example 4. In addition, even if the dental prosthesis of Example 4 is fractured, fractures tend not to be scattered.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A dental prosthesis comprising:
   a substrate body comprising titanium; and
   a molding body comprising a crystallized glass which is molded on a part of the substrate body to form a shape corresponding to at least a crown of a tooth, said crystallized glass having a thermal expansion coefficient of $\pm 5 \times 10^{-7}$ with respect to the titanium,
   wherein the molding body is chemically bonded to the substrate body.

2. The dental prosthesis according to claim 1, wherein said substrate body is pure titanium whose surface is coated with a material selected from the group consisting of titanium nitride, titanium carbonitrate, and titanium oxide.

3. The dental prosthesis according to claim 2, wherein the chemical bond between said substrate body and said molding body is such that either nitrogen or oxygen atoms contained in a layer comprising one of titanium nitride, titanium carbonitride, and titanium oxide covering the surface of the pure titanium, or oxygen atoms contained in a surface layer of said crystallized glass are bonded to either titanium or silicon atoms contained in an opposite layer.

4. The dental prosthesis according to claim 2, wherein the crystallized glass includes both a mica crystal and a β-spodumere crystal.

5. The dental prosthesis according to claim 4, wherein the crystallized glass has a thermal expansion coefficient of $8.2 \times 10^{-6}$.

6. The dental prosthesis according to claim 2, wherein the pure titanium is coated with titanium nitride.

7. The dental prosthesis according to claim 1, wherein the chemical bond between said substrate body and said molding body is such that atoms contained in a surface layer of said titanium constituting said substrate body or atoms contained in a surface layer of said crystallized glass constituting said molding body are bonded to titanium atoms or silicon atoms present in an opposite surface layer.

8. A dental prosthesis comprising:
a substrate body comprising titanium which is pure titanium whose surface is coated with a material selected from the group consisting of titanium carbonitrate and titanium oxide; and
a molding body comprising a crystallized glass which is molded on a part of the substrate body to form a shape corresponding to at least a crown of a tooth, said crystallized glass having a thermal expansion coefficient of $\pm 5 \times 10^{-7}$ with respect to the titanium, wherein the molding body is chemically bonded to the substrate body.

9. The dental prosthesis according to claim 8, wherein the chemical bond between said substrate body and said molding body is such that either nitrogen or oxygen atoms contained in a layer comprising one of titanium carbonitride, and titanium oxide covering the surface of pure titanium, or oxygen atoms contained in a surface layer of said crystallized glass are bonded to either titanium or silicon atom contained in an opposite layer.

10. The dental prosthesis according to claim 9, wherein the substrate body is pure titanium coated with titanium carbonitrate.

11. The dental prosthesis according to claim 9, wherein the substrate body is pure titanium coated with titanium oxide.

* * * * *